United States Patent [19]

Müller

[11] 4,207,309

[45] Jun. 10, 1980

[54] PHENYLISOQUINOLINE DERIVATIVES AS DIAGNOSTIC AGENTS

[76] Inventor: Eugenio E. Müller, Via Mangiagalli, 5, Milano, Italy

[21] Appl. No.: 953,177

[22] Filed: Oct. 20, 1978

[30] Foreign Application Priority Data

Feb. 16, 1978 [IT] Italy ................. 20307 A/78

[51] Int. Cl.$^2$ ............... A61K 29/00; A61K 31/47; G01N 33/16
[52] U.S. Cl. ........................... 424/9; 424/258
[58] Field of Search ........................ 424/9, 258

[56] References Cited

PUBLICATIONS

Müller et al., J. of Clin. Endocrin. & Metab. vol. 47, No. 6, 1978, pp. 1352–1357.
Scanlon et al., Chem. Abs. vol. 88, 1978, Ab. No. 99271r.

*Primary Examiner*—Anna P. Fagelson

[57] ABSTRACT

Derivatives of phenylisoquinoline, in particular 8-amino-2-methyl-4-phenyl-1,2,3,4-tetrahydro-iso-quinoline hydrogen maleate, are used as effective agents in the differential diagnosis of disorders of hypothalamo-pituitary function. The phenylisoquinoline derivatives are administered orally at a dose of about 1–5 mg/body wt. in order to differentiate between "functional" and "organic" (tumorous) diseases.

1 Claim, No Drawings

PHENYLISOQUINOLINE DERIVATIVES AS DIAGNOSTIC AGENTS

BACKGROUND OF THE INVENTION

1. Field of the invention

The present invention deals with the utilization of phenylisoquinoline derivatives and, namely, of 8-amino-2-methyl-4-phenyl-1,2,3,4-tetrahydro-iso-quinoline hydrogen maleate (Nomifensine, Alival, Hoechst) and its derivatives in the differential diagnosis of disorders of hypotalamo-pituitary function.

2. Description of the prior art

The importance of some chemical agents as effective and suitable tools for the diagnosis of disease states is a well recognized event. In particular, the use of chemical agents in in vitro and/or in vivo test systems is of great aid for establishing whether certain symptoms may be attributed to a simple dysfunctional state or to an organic disturbance. In these instances, the use of appropriate diagnostic agents allows to clarify the etiology of the disturbance and hence to initiate the appropriate therapeutic trial.

In the last few years the studies of the central mechanisms involved in the regulation of anterior pituitary (AP) hormone secretion have led to the introduction of several functional tests in clinical practice. These tests are mainly based on:

(1) the use of neuroactive compounds, which are capable to affect the metabolism of neurotransmitters involved in the neuroendocrine control of AP function or, (2) of hypothalamic regulatory hormones which exert their action directly at AP level.

From a theoretical ground, combined use of neuroactive drugs and hypothalamic hormones would be capable of unravelling the primary site(s) in the central nervous system (CNS) or/and the pituitary where the endocrine disturbance is located. This event, however, does not constantly occur, firstly, for the ability of the neuroendocrine drugs to affect also the AP gland, secondly, since the hyperplastic or tumoral pituitary may evidence receptors for the neuroactive drugs which are normally lacking in the intact AP gland, thirdly, as often the pathologic AP tissue is capable of responding normally to the hypophysiotropic stimuli.

Therefore, the diagnosis on the type and, hence, site(s) of the disturbance, quite often of paramount import for the prognosis and for a correct therapeutic approach cannot be made or, alternatively, is made only too late, when the alteration has already progressed too much.

The here-in-above mentioned difficulties, i.e. of developing (or possessing) effective diagnostic agents are even more apparent in the case of disturbances of the hypotalamo-pituitary system, on considering the multiple interactions existing between this neuroendocrine system and the rest of the body.

Thus, concomitant evaluation of AP hormone secretion in resting state or following administration of hypothalamic hormones (i.e. LH—RH) has been discouraging with regard to the differentiation between functional or pathologic states. A low basal plasma LH level concomitant to a blunted LH response to LH—RH in highly suggestive of a pituitary tumor in cases of hypogonadism, galactorrhea and hyperprolactinemia; however, even a normal LH and FSH response to LH—RH does not rule out the existence of a pituitary tumor. In hyperprolactinemic patients with pituitary microadenomas there is quite often an exaggerated FSH response to LH—RH; however, such an exaggerated FSH response reportedly is present also in some amenorrhea-galactorrhea patients with hyperprolactinemia but with no evidence of pituitary tumor.

The differential diagnosis between functional and pathologic states is further compounded by the fact that many cases originally classified as "functional" because of the finding of a radiologically normal pituitary fossa may be actually due to pituitary microadenomas.

From the foregoing it appears that until now, no functional test or series of tests have been introduced which allow a clear-cut differentation between "functional" or tumorous hyperprolactinemia, in spite of the fact that the usefulness of possessing neuroactive drugs capable of affecting central monoaminergic neurotransmission but unable to act directly at the level of receptor sites located on a normal or pathologic AP is cleraly emerging.

SUMMARY OF THE INVENTION

I have now discovered and this is the object of this invention that 8-amino-1,2-3,4-tetrahydro-2-methyl-4-phenyliso-quinoline hydrogen maleate (Hoe/948) or Nomifensine, is capable of acting as an useful diagnostic agent in disturbances of the hypothalamo-pituitary system. Nomifensine is a drug used for its antidepressant properties which acts mainly by inhibiting the reuptake of dopamine (DA) and norepinephrine (NE) at presynaptic sites and in part by releasing DA at postsynaptic sites; instead it is unable to affect directly DA receptor sites.

Nomifensine, according to the present invention, has proved to be a neuropharmacologic agent capable of differentiating between functional and tumorous hyperprolactinemia.

Before referring on the methodology used and on the results obtained, it appears suitable the knowledge of the diagnostic difficulties encountered in syndromes characterized by an altered prolactin (PRL) secretion from the AP gland.

Hyperprolactinemic states in humans are commonly subdivided between "functional" mainly due to:

(1) prolonged use of contraceptive drugs;
(2) amenorrhea and galactorrhea post-partum (Chiari-Frommel syndrome);
(3) idiophatic amenorrhea and galactorrhea;
(4) puerperium;
(5) hypothyroidism;
(6) chronic renal failure;
(7) iatrogenic origin;

and "organic" mainly represented by hypothalamic and/or pituitary tumors.

Many functional tests have been introduced in clinical practice with the aim of differentiating between hyperprolactinemia due to pituitary tumors and the "functional" cases.

The most frequently "stimulation tests" used so far include acute administration of: (1) TRH; (2) chlorpromazine; (3) sulpiride. The results obtained indicate that there is no single provocative test able to distinguish between tumorous and functional hyperprolactinemia, though, negative responses are more frequently encountered in patients, with PRL-secreting tumors.

The inhibition tests used so far consist in the administration of DA agonist drugs e.g., L-DOPA and 2-Br-α- ergocryptine (CB 154). These inhibition tests are equally unable to distinguish between tumors and "functional" cases. For instance L-DOPA reduced circulating PRL levels by 50% in about half of patients investigated, without any appreciable difference between "functional" and tumorous cases, and CB 154 too was unable of such differentiation, even though it proved to be more effective than L-DOPA in lowering plasma PRL levels.

Although the inhibitory role of the dopaminergic system(s) in the control of PRL secretion has been unequivocally established it is still under debate whether a PRL-inhibiting factor (PIF), whose activity is tonically stimulated by dopaminergic neurons, exists in the hypothalamus or whether instead the PIF activity of the hypothalamus may be entirely accounted by brain DA. Dopamine released from tubero-infundibular dopaminergic (TIDA) nerve terminals into the hypophysial portal circulation may act directly at the level of the AP, where receptor sites for DA have been located.

Direct DA agonist drugs (apomorphine, piribedil, ergot drugs, etc.) may thus inhibit PRL release either indirectly by stimulation of DA receptors (in the tuberoinfundibular DA system?) which then release PIF or by direct stimulation of DA receptors located on the lactotrophs. Even though the main site of action of these compounds in presently unknown, from a theoretical viewpoint a central nervous system and/or a pituitary site(s) of action can be postulated.

Therefore, since these drugs possess a double site of action i.e., the CNS and the AP, they are unable to differentiate between a CNS or a pituitary etiology as the cause of hyperprolactinemia.

The same conclusion does not hold true for drugs capable of enhancing dopaminergic neurotransmission without directly affecting DA receptor sites e.g., drugs capable of inhibiting DA reuptake. Since their ability to activate dopaminergic neurotransmission appears to be unrelated to direct stimulation of postsynaptoc DA receptors, but instead involves presynaptic events, they should be effective, even though not necessarily, to inhibit PRL secretion in the healthy subjects or in the so called "functional" hyperprolactinemia, conditions in which a presynaptic pool of DA available for release is expected to be present, and, respectively, ineffective to lower PRL secretion, in hyperprolactinemic states due to a primitive tumor of pituitary lactotrophs. It is known, in fact, that the normal or pathologic mammalian pituitary does not contain the presynaptic neuronal component through which an activation of the postsynaptic catecholamine (CA) receptors occurs physiologically. Thus, drugs which block DA reuptake should be unable to affect DA receptor sites located at AP level. The possibility that the action of such drugs may be exerted at the level of the median eminence by inhibiting the uptake of DA which is normally released into the portal circulation has to be considered but appears to be unlikely. In fact, granted that DA is normally released into the portal circulation it is conceivable that presynaptic capture of the released DA does not play at this level a major role in the inactivation of the neurotransmitter.

On the ground of the rationale above described, the present invention will be illustrated in more detail mentioning a series of experiments performed in man with altered PRL secretion; the results obtained do indicate that Nomifensine is capable of differentiating between "functional" and pathologic cases of hyperprolactinemia.

Studies with Nomifensine in the Human (Table 1–6)

1—Puerperium a. Nomifensine (100 mg po) was administered to 7 puerperal hyperprolactinemic women (post partum day 2) and blood samples were taken at 30 min intervals for 240 min, for determination of PRL in the plasma.

Administration of Nomifensine was accompanied by inhibition of plasma PRL levels (at least 50% at 210–240 min). No untoward side effects were noticed (Table 2).

b. Nomifensine (200 mg po) was administered to 4 puerperal hyperprolactinemic women (post-partum day 2). No noticeable difference was present in the PRL-lowering effect of the drug at this dose in comparison with the 100 mg dose, except that the PRL-lowering effect was manifested earlier (50% inhibition at 150 min). No untoward side effects were noticed. (Table 3).

c. In one subject who was taking since 2 months metoclopramide, a blocker of DA receptors, administration of Nomifensine (200 mg po) was followed by a clear-cut reduction in plasma PRL levels (about 5% inhibition starting from 150 min). (Table 4, patient D.A.).

d. In 2 subjects with a trend towards raised baseline PRL levels but no evidence of an endocrinopathy, administration of Nomifensine (200 mg po) resulted in marked inhibition of plasma PRL levels (at least 50%). (Table 4, patients L.R. and A.F.).

e. In 2 normal subjects, administration of Nomifensine (200 mg po) did not modify baseline plasma PRL levels; in a third subject it induced instead a reduction of plasma PRL greater than 50% at 150 min; (Table 4).

2—Pathologic hyperprolactinemia

Nomifensine was administered in 10 subjects with pathologic hyperprolactinemia (primary or secondary amenorrhea, galactorrhea) (9 cases out of 10). In 7 subjects with radiological evidence of alterations in the sella turcica (enlargement of double profile), administration of Nomifensine (100 or 200 mg po) did not alter plasma PRL levels (maximum inhibition 36% at 180 min in 1 subject (M.M.) with a 100 mg dose). In 6 of these subjects the administration of CB 154 (2.5 or 5.0 mg po) induced instead a striking inhibition in plasma PRL levels (80% inhibition at 210–300 min). (Tables 5 and 6).

In 3 subjects (baseline PRL levels 60 ng/ml), of whom 1 with no radiological evidence of alterations in the sella turcica, 2 others without this examen being performed, administration of Nomifensine (200 mg po) did not appreciably change plasma PRL levels (maximum inhibition 13% at 180 min in 1 subject). One of these subjects (B.L.) proved to be completely refractory to administration of Nomifensine at the dose of 300 mg po (Table 6).

TABLE 1

Clinical and laboratory details in patients with hyperprolactinemic amenorrhea

| Case | Age | Ameno-rrhea[a] | GA[b] | OBST. AN.[c] | Rx Sella Turcica | Plasma PRL (ng/ml) (range)[e] | Plasma LH(mµ/ml) Basal (range)[e] | Plasma LH(mµ/ml) After LH-RH (ΔLH) | Plasma FSH (mµ/ml) Basal (range)[e] | Plasma FSH (mµ/ml) After LH-RH (ΔFSH) | E$_2$[f] (pg/ml) | P[g] (pg/ml) |
|---|---|---|---|---|---|---|---|---|---|---|---|---|
| M.M. | 26 | S(2 yrs) | + | NBC[d] | Enlarged | 50–80 | 6–10 | — | 8–14 | — | 96 | 255 |
| P.B. | 30 | S(5 yrs) | + | NBC | Double profile | 230–375 | 4–7 | 24 | 3–10 | 13.2 | 12 | 185 |
| C.G. | 19 | S(1 yr) | + | NBC | Small | 50–64 | 5–20 | 9.8 | 8–14 | 8.0 | — | — |
| B.L. | 22 | S(3 yrs) | — | NBC | — | 48–60 | 1–8 | 28 | 7–11 | 10.2 | 12 | 370 |
| Z.G. | 41 | S(15 yrs) | + | NBC | Enlarged | 250–350 | 7–10 | 42 | 14–20 | 28 | 56 | 664 |
| P.S. | 21 | P | + | NBC | — | 54–60 | — | — | — | — | — | — |
| P.A. | 19 | Polimen (5 yrs) | + | NBC | Enlarged | 125–170 | 3–8 | — | 11–23 | — | 120 | 600 |
| D.A. | 35 | S(8 mos) metoclopr. (2 mos) | ++ |  | Normal | 25–55 55–80 | 6–8 | — | 7–8 | — | 110 | 900 |
| G.G. | 34 | S(2 yrs) | + | NBC | Double profile | 28–55 | — | — | — | — | — | — |
| P.I. | 38 | S(20 yrs) | ± | E+p[h] | Enlarged | 132–156 | 2.4 ng/ml | — | — | — | — | — |
| F.M. | 28 | S(3 yrs) | + | NBC | Double profile | 44–65 | — | — | — | — | 66 | 500 |

[a] S = Secondary; P = Primary;
[b] GA = Galactorrhea;
[c] OBST.AN. = Obstetrics Anamnesis;
[d] NBC = Negative;
[e] Control values in early follicular phase: PRL (8.0–12.0 ng/ml); LH (5.9 ± 1.1 mµ/ml); FSH (11.3 ± 2.2 mµ/ml);
[f] E$_2$ = Estradiol;
[g] P = Progesterone;
[h] E+P = Estrogens + Progesterone.

TABLE 2

Effect of Nomifensine (100 mg po) on plasma prolactin (ng/ml) in puerperal subjects*

| Case | −30 | 0 | 30 (S/B) | 60 (S/B) | 90 (S/B) | 120 (S/B) | 150 (S/B) | 180 (S/B) | 210 (S/B) | 240 (S/B) |
|---|---|---|---|---|---|---|---|---|---|---|
| C.P. | 250 | 240 | 245 (1.0) | 240 (0.98) | 100 (0.41) | 70 (0.29) | 75 (0.30) | — | 110 (0.45) | 130 (0.53) |
| P.M.B. | 135 | 200 | 245 (1.46) | 195 (1.16) | 210 (1.25) | 90 (0.53) | 210 (1.25) | 72.5 (0.43) | 45 (0.26) | 40 (0.23) |
| P.L. | 180 | 150 | 130 (0.78) | 120 (0.73) | 180 (1.1) | 110 (0.66) | 110 (0.66) | 120 (0.73) | 145 (0.88) | 135 (0.80) |
| P.I. | 210 | 205 | 180 (0.86) | 150 (0.72) | 122 (0.58) | 120 (0.57) | 95 (0.45) | 100 (0.48) | 115 (0.55) | 112 (0.53) |
| M.R. | 185 | 150 | 145 (0.86) | 145 (0.86) | 140 (0.83) | 157 (0.93) | 125 (0.74) | 120 (0.71) | 112 (0.66) | 142 (0.84) |
| C.G. | 270 | 225 | 225 (0.90) | 160 (0.64) | 130 (0.52) | 147 (0.59) | 165 (0.65) | 125 (0.50) | 75 (0.30) | 35 (0.12) |
| V.R. | 225 | 240 | 290 (1.24) | 270 (1.15) | — | — | — | — | 137 (0.58) | 102 (0.43) |

*Post-partum days 2

TABLE 3

Effect of Nomifensine (200 mg po) on plasma prolactin (ng/ml) in puerperal subjects*

| Case | −30 | 0 | 30 (S/B) | 60 (S/B) | 90 (S/B) | 120 (S/B) | 150 (S/B) | 180 (S/B) | 210 (S/B) | 240 (S/B) | 300 (S/B) |
|---|---|---|---|---|---|---|---|---|---|---|---|
| N.N. | 220 | 200 | 800(0.85) | 160(0.76) | 155(0.73) | 145(0.69) | 155(0.73) | 140(0.66) | 140(0.66) | 135(0.64) | 205(0.98) |
| E.G. | 165 | 190 | 150(0.84) | 110(0.62) | 90(0.50) | 95(0.53) | 60(0.34) | 62.5(0.35) | 55(0.31) | 65(0.37) | 72.5(0.41) |
| A.B. | 170 | 160 | 160(0.94) | 140(0.82) | 100(0.58) | 140(0.82) | — | 145(0.85) | 160(0.94) | 145(0.85) | 90(0.53) |
| C.P. | 240 | 245 | 240(0.98) | 210(0.86) | 175(0.72) | 100(0.41) | 95(0.39) | — | 100(0.41) | 110(0.45) | 130(0.53) |

*Post-partum days 2

TABLE 4

Effect of Nomifensine (200 mg po) on plasma PRL in patients with iatrogenic or functional hyperprolactinemia or normal subjects (NS)

| Case | −30 | 0 | 30 (S/B) | 60 (S/B) | 90 (S/B) | 120 (S/B) | 150 (S/B) | 180 (S/B) | 210 (S/B) | 240 (S/B) | 300(S/B) |
|---|---|---|---|---|---|---|---|---|---|---|---|
| D.A. | 35 | 25 | 13(0.50) | 18.5(0.61) | 17.0(0.56) | 16.0(0.53) | 3(0.10) | 3(0.10) | 3(0.10) | 3(0.10) | 3(0.10) |
| L.R. | 17.5 | 12.0 | 14(0.95) | 12.5(0.84) | *9.5(0.64) | 9.0(0.61) | 8.5(0.57) | 7.5(0.51) | 7.7(0.52) | 7.7(0.52) | 12.0(0.81) |
| A.F. | 15.5 | 9.7 | 6.5(0.51) | 5.8(0.46) | — | 4.6(0.36) | 5.3(0.42) | 5.0(0.39) | 5.2(0.41) | — | 6.0(0.47) |
| NS |  |  |  |  |  |  |  |  |  |  |  |
| M | 10.8 | 9.0 | 8.6(0.86) | — | 9.0(0.90) | 9.0(0.90) | 8.5(0.85) | — | — | — | — |
| F | 5.6 | 7.5 | 12(1.83) | 6.6(1.01) | 8.5(1.29) | 6.3(0.96) | 6.1(0.93) | 6.5(1.0) | 7.5(1.14) | 6.2(0.94) | 6.4(0.97) |
| F | 9 | 9 | 7.2(0.96) | 8(1.06) | 4(0.53) | 5.5(0.73) | 3.2(0.42) | 3.8(0.50) | 5.3(0.70) | 5(0.66) | 8(1.06) |

M = Male
F = Female

TABLE 5

Effect of Nomifensine (100* or 200**/mg po) or CB 154 (2.5* and 5* mg po) on plasma prolactin (ng/ml) in patients with hyperprolactinemic amenorrhea

| Case | −30 | 0 | 30 (S/B) | 60 (S/B) | 90 (S/B) | 120 (S/B) | 150 (S/B) | 180 (S/B) | 210 (S/B) | 240 (S/B) | 300 (S/B) |
|---|---|---|---|---|---|---|---|---|---|---|---|
| M.M.* | 100 | 68 | 58(0.69) | 58(0.69) | 58(0.69) | 56(0.66) | 50(0.59) | 54(0.64) | 62(0.73) | 62(0.73) | 50(0.59) |
| M.M.** | 74 | 62.5 | 65(0.95) | 65(0.95) | — | 60(0.88) | 55(0.80) | 67.5(0.99) | 67.5(0.99) | 55(0.80) | 65(0.95) |
| M.M.* | 80 | 78 | 72(0.91) | 64(0.81) | 48(0.62) | 64(0.81) | 40(0.50) | 28(0.34) | 22(0.27) | 19(0.24) | 15(0.19) |
| P.B.* | 275 | 250 | 250(0.95) | 250(0.95) | 255(0.97) | 245(0.93) | 245(0.93) | 250(0.95) | 250(0.95) | 245(0.93) | 300(1.14) |
| P.B.** | 375 | 350 | 350(1.00) | 350(1.00) | 375(1.07) | 325(0.92) | 325(0.92) | 350(1.00) | 310(0.88) | 310(0.88) | 400(1.14) |
| P.B.* | 310 | 305 | 290(0.94) | 275(0.89) | 264(0.86) | 135(0.44) | 160(0.52) | 155(0.50) | 85(0.27) | 65(0.21) | 65(0.21) |
| Z.G.** | 250 | 275 | 230(0.87) | 220(0.84) | 210(0.80) | 220(0.84) | 210(0.80) | 180(0.68) | 250(0.95) | 210(0.80) | 200(0.76) |
| Z.G.* | 275 | 275 | 240(0.87) | 200(0.72) | 160(0.58) | 115(0.42) | 100(0.36) | 85(0.31) | 70(0.25) | 57.5(0.20) | 52.5(0.19) |
| G.G.** | — | 28 | 27(0.96) | 31(1.10) | 29(1.03) | 26(0.92) | 27(0.96) | 30(1.07) | 27(0.96) | 28(1.00) | — |
| G.G.* | — | 35 | 34(0.97) | 27(0.77) | 18(0.51) | 15(0.42) | 14(0.40) | 11(0.31) | — | — | — |
| P.I.** | — | 156 | 136(0.87) | 144(0.92) | 156(1.00) | 124(0.79) | 144(0.92) | 164(1.05) | 144(0.92) | 140(0.89) | — |
| P.I.* | — | 152 | 148(0.97) | 128(0.84) | 80(0.52) | 64(0.42) | 40(0.26) | 36(0.23) | 28(0.18) | 24(0.15) | — |
| F.M.** | — | 55 | 55(1.00) | 55(1.00) | 55(1.00) | 52(0.94) | 50(0.90) | 50(0.90) | 57(1.03) | 62(1.12) | — |
| F.M.* | — | 44 | 56(1.27) | 36(0.81) | 40(0.90) | 28(0.63) | 24(0.54) | 20(0.45) | — | — | — |

TABLE 6

Effect of Nomifensine (100*, 200 or 300* mg po) on plasma PRL (ng/ml) in patients with hyperprolactinemic amenorrhea

| Case | −30 | 0 | 30(S/B) | 60(S/B) | 90(S/B) | 120(S/B) | 150(S/B) | 180(S/B) | 210(S/B) | 240(S/B) | 300(S/B) |
|---|---|---|---|---|---|---|---|---|---|---|---|
| P.A.* | 150 | 170 | 150(0.93) | 150(0.93) | 135(0.84) | 160(1.0) | 160(1.0) | 160(1.0) | 145(0.90) | 145(0.90) | 145(0.90) |
| C.G.** | 64 | 64 | 64.5(1.0) | 65(1.01) | 62.5(0.97) | 63(0.98) | 63(0.98) | 56(0.87) | 57(0.89) | 56.5(0.89) | 62.5(0.97) |
| B.L.** | 58 | 58 | 50(0.86) | 54(0.93) | 54(0.93) | 55(0.94) | 54(0.93) | 54(0.93) | 58(1.00) | 55(0.94) | 54(0.93) |
| B.L.*** | 48 | 44 | 44(0.95) | 44(0.95) | 44.5(0.96) | 44(0.95) | 48(1.04) | 44(0.95) | 44(0.95) | 42(0.91) | 42(0.91) |
| P.S.** | 60 | 54 | 54(0.94) | 52(0.91) | 55(0.96) | 52(0.94) | 54(0.94) | 50(0.87) | 52(0.91) | — | 53(0.92) |

From the data reported in the Tables it appears that Nomifensine proved to be effective in lowering plasma PRL levels in 11 subjects with the "functional" hyperprolactinemia of the puerperium and in 1 case of iatrogenic hyperprolactinemia. Nomifensine was active also in two subjects with a trend towards higher baseline plasma PRL but no signs of endocrinopathy and in 1 out of 3 normal subjects.

In contrast, it proved to be ineffective in 7 subjects with radiological evidence of alterations of the sella turcica, and in 3 subjects for whom the existence of such alterations was not evident; in 1 of these subjects the existence of a PRL-secreting tumor was suggested by the presence of a reduced gonadotropin secretion (B.L.).

Collectively, on the basis of these findings it would appear that Nomifensine is a neuropharmacologic tool valuable for differentiating between functional and tumorous hyperprolactinemia. Its use might be particularly suitable for the early diagnosis of small pituitary tumors (microadenoma), which may cause no radiological expansion of the fossa.

Use of Nomifensine in other disorders of the hypothalamo-pituitary system

Although the diagnostic use of Nomifensine is presently mainly envisaged in states of hyperprolactinemia, the possibility exists for a profitable use of the drug also in other disorders of the hypothalamo-pituitary system.

Since Nomifensine is capable to block the presynaptic uptake of both DA and NE, it may be used for evaluating pituitary growth hormone (GH) response in growth disturbances. Among the functional tests for evaluating the GH secretory capacity, an important role is played by the L-DOPA test. L-DOPA, which is the physiologic precursor of both CA's, NE and DA, is capable to induce an enhanced GH release through a CNS mediated mechanism (activation of catecholaminergic neurotransmission) and allows to determine whether a subject with a growth disturbance, whose baseline GH levels are undetectable, is capable or not of giving a sufficient pituitary GH response. On the other hand, the existence of a marked individual variability of the GH response to L-DOPA is a well known phenomenon so that a diminished GH response to this drug far from reflecting the existence of a reduced pituitary capacity for GH, may be due to an individual refractoriness to catecholaminergic stimulation. As previously mentioned, Nomifensine blocks both NE and DA re-uptake; thus combined Nomifensine-L-DOPA administration would allow a more potent activation of post-synaptic CA receptor sites and permit to differentiate clearly the individuals who are GH deficient from those who respond poorly to the L-DOPA stimulus, not for a pituitary deficit, but for a reduced individual responsiveness of the CNS to the latter.

Proofs that Nomifensine alone is capable to stimulate GH release have been obtained by the applicant in the dog at the dose of 7 mg/10 kg B.W. i.v., and in man after oral administration of 200 mg; in acromegalic subjects, Nomifensine, (75 mg po), has been unable to modify the elevated baseline GH levels. Although for having more definitive conclusions on the effect of Nomifensine in acromegaly the use of higher doses of the drug (200–300 mg) is mandatory, the ability of Nomifensine to enhance GH release in healthy subjects and its inefficacy in acromegalic patients is at variance with the neuroendocrine profile of direct DA-agonist drugs (i.e., apomorphine, CB 154, piribedil), which are effective both in healthy subjects (GH-stimulation-CNS action) and in acromegalic patients (GH inhibition-pituitary action).

Therefore, the drug might be usefully employed in acromegaly for differentiating those cases in whom a functional connection between the CNS and the AP function is still present (enhanced GH release following Nomifensine) from those in which no functional links are present and the tumor functions autonomously (unaltered GH levels following Nomifensine). An useful means would thus be available capable of providing information on the functional evolution of the endocrine dysfunction.

It is well known that in Cushing's disease, a pathologic state with hypercortisolemia associated with adrenocortical hyperplasia and excessive ACTH secretion, in the presence or in absence of a pituitary-secreting tumor, CB 154 is capable of reducing plasma ACTH titers. In those cases of Cushing's disease in which hypercortisolism results from an hyperplastic or tumoral AP gland, Nomifensine is expected to be ineffective to lower circulating ACTH levels. Instead, were ACTH hypersecretion due to a primitive hyperfunctioning of the CRF-secreting system, on the ground of the present knowledge on the inhibitory role of catecholaminergic stimulation on ACTH release, a lowering effect of Nomifensine on circulating ACTH levels may be foreseen.

Although the present invention refers in particular to Nomifensine, it is apparent that the same can be applied to metabolic products of the drug such as 4'-hydroxy-nomifensine, 3'-methoxy-4'-hydroxy-nomifensine and 3'-hydroxy-4'-methoxy-nomifensine.

What I claim is:

1. A method of differentiating between functional and pathological cases of hyperprolactinemia which comprises orally administering to a patient a unitary dosage of 100–300 mg of a compound selected from the group consisting of 8-amino-2-methyl-4-phenyl-1,2,3,4-tetra-hydro-iso-quinoline hydrogen maleate (nomifensine); 4'-hydroxy-nomifensine; 3'-methoxy-4'-hydroxynomifensine and 3'-hydroxy-4'-methoxy-nomifensine, and thereafter measuring the plasma prolactin level of said patient.

* * * * *